Figure 1:
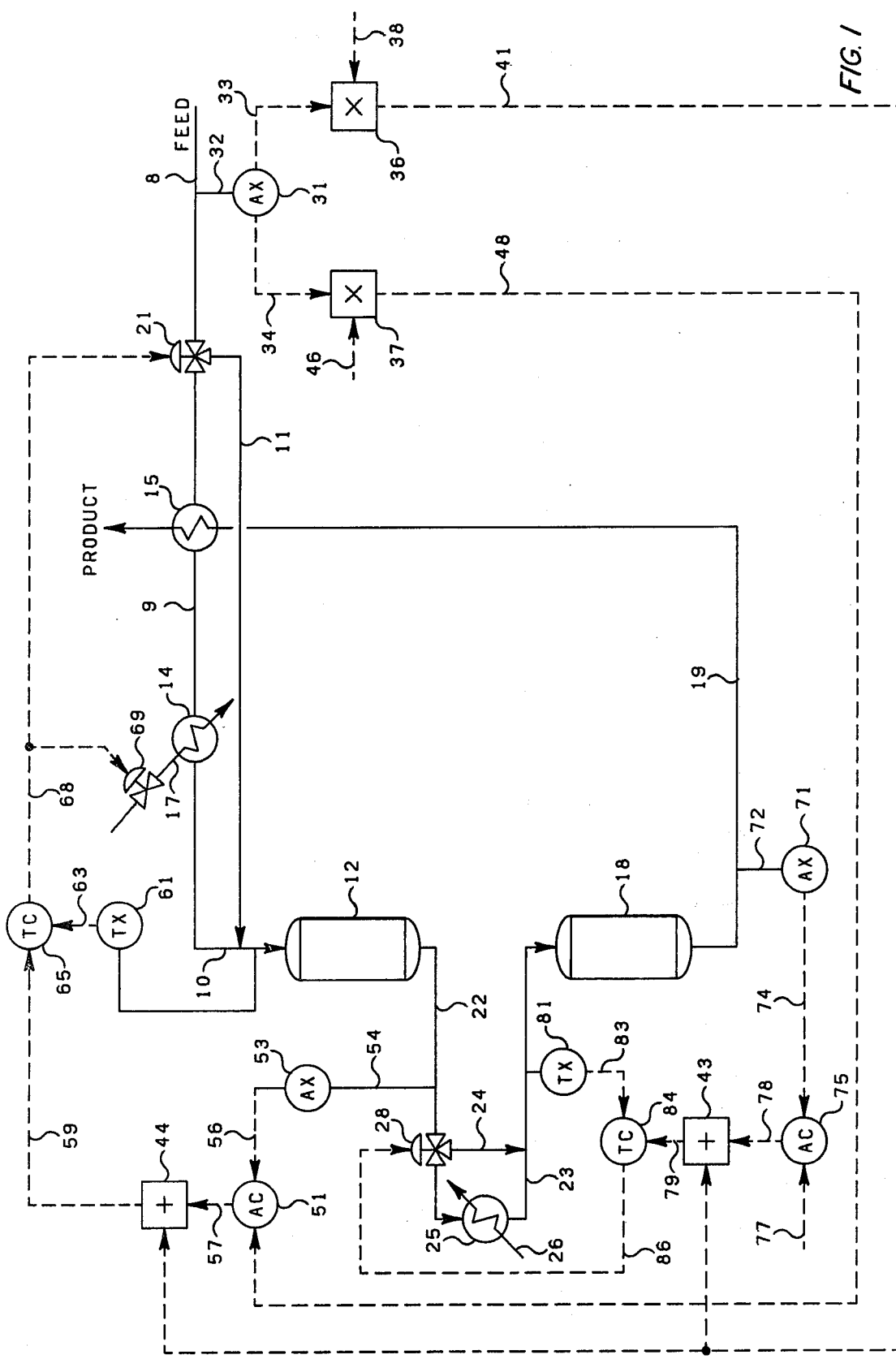

United States Patent [19]

Kelley

[11] 4,234,410

[45] Nov. 18, 1980

[54] TEMPERATURE CONTROL OF EXOTHERMIC REACTIONS

[75] Inventor: Carl S. Kelley, Bartlesville, Okla.

[73] Assignee: Phillips Petroleum Company, Bartlesville, Okla.

[21] Appl. No.: 23,355

[22] Filed: Mar. 23, 1979

[51] Int. Cl.³ .......................... B01J 8/04; C07C 7/167
[52] U.S. Cl. .............................. 208/57; 208/DIG. 1; 364/500; 422/289
[58] Field of Search ........................... 208/57, DIG. 1; 364/500; 422/189; 585/259, 500, 841, 956, 263

[56] References Cited

U.S. PATENT DOCUMENTS

| | | | |
|---|---|---|---|
| 3,196,189 | 7/1965 | Ogle et al. ............................ 585/501 |
| 3,441,626 | 4/1969 | Kelley ................................. 585/259 |
| 3,471,582 | 10/1969 | Lupfer ................................. 208/143 |
| 3,656,911 | 4/1972 | Hobbs ................................. 585/500 |
| 3,839,483 | 10/1974 | Carr et al. ............................ 208/143 |
| 4,132,529 | 1/1979 | Schwimmer .......................... 208/146 |

Primary Examiner—H. Levine

[57] ABSTRACT

In a selective hydrogenation process wherein at least two catalyst beds in series are utilized, the temperature of the feed stream to the first catalyst bed and the temperature of the feed stream from the first catalyst bed to the second catalyst bed is controlled so as to maintain a desired reaction temperature in both catalyst beds and to maintain a desired relationship between the amount of the impurity selectively hydrogenated in the first catalyst bed and the amount of the impurity selectively hydrogenated in the second catalyst bed.

36 Claims, 1 Drawing Figure

TEMPERATURE CONTROL OF EXOTHERMIC REACTIONS

This invention relates to temperature control of an exothermic reaction. In a specific aspect this invention relates to selective hydrogenation of unsaturated hydrocarbons in mixed hydrocarbon streams. In another specific aspect this invention relates to selective hydrogenation of acetylenic compounds in olefin-rich hydrocarbon streams.

In many exothermic chemical reactions it is necessary to control temperature within certain limits in order to maintain satisfactory yields and to prevent side reactions. This is particularly true in selective hydrogenation processes. For example, ethylene is commonly produced by the thermal cracking of hydrocarbon feedstocks. Unfortunately, some acetylene is also produced, and must be removed for many applications. This can be accomplished by selective catalytic hydrogenation of the acetylene.

In selective hydrogenation operations of this type, it is quite important to maintain the operating temperature within narrow limits. If the temperature is too low, the hydrogenation reaction is not carried out in a sufficiently complete manner to remove the acetylene. If the temperature becomes too high, side reactions such as the hydrogenation of ethylene and the formation of polymers may result. It is also very important to prevent excessive temperatures from being reached because of the danger of explosions.

It is also important, where two catalyst beds or reaction zones in series are utilized as in the present invention, to maintain a relationship between the percentage of the acetylene hydrogenated in the first catalyst bed and the percentage of the acetylene hydrogenated in the second catalyst bed. Preferably the first catalyst bed is utilized to hydrogenate most of the acetylene with the second catalyst bed being utilized primarily as a cleanup process. Close control of the percentage of the acetylene hydrogenated in each catalyst bed provides for a more efficient conversion of acetylene and reduces the risk of excessive temperature in either catalyst bed.

It is thus an object of this invention to provide method and apparatus for controlling the reaction temperature of an exothermic chemical reaction process. Another object of this invention is to provide method and apparatus for controlling the selective hydrogenation of unsaturated hydrocarbons in mixed hydrocarbon streams. Still another object of this invention is to provide method and apparatus for controlling the selective hydrogenation of acetylenic compounds in olefin-rich hydrocarbon streams.

In accordance with the present invention, a selective hydrogenation process which utilizes two catalyst beds or reaction zones in series is controlled so as to maintain a desired reaction temperature in each catalyst bed and to maintain a desired relationship between the amount of material selectively hydrogenated in the first catalyst bed and the amount of material selectively hydrogenated in the second catalyst bed. Two separate reactors may be utilized or a single reactor with two catalyst beds may be utilized so long as control and analysis of the fluid stream flowing between the two catalyst beds is possible. Hereafter, the term first reactor and second reactor is utilized to describe the invention but the invention is not limited to the use of separate reactor vessels.

The feed stream to the first reactor and the feed stream from the first reactor to the second reactor are split into at least two portions. A first portion of the feed stream to the first reactor is heated before being passed to the first reactor. A second portion of the feed stream to the first reactor is utilized as a quench fluid and is introduced into the first portion of the feed stream to the first reactor after the first portion of the feed stream to the first reactor has been heated. A first portion of the feed stream from the first reactor to the second reactor is supplied directly to the second reactor. A second portion of the feed stream from the first reactor to the second reactor is cooled and is utilized as a quench fluid by being introduced into the first portion of the feed stream from the first reactor to the second reactor before the feed stream enters the second reactor.

An analysis of the feed stream flowing to the first reactor is utilized to provide an indication of the amount of acetylene in the feed stream and also an indication of the amount of carbon monoxide in the feed stream. An analysis of the feed stream flowing from the first reactor to the second reactor is utilized to provide an indication of the amount of acetylene in the feed stream flowing from the first reactor to the second reactor. Based on the analysis of the amount of acetylene in the feed stream flowing to the first reactor and the analysis of the amount of acetylene in the feed stream flowing from the first reactor, the temperature of the feed stream flowing to the first reactor is controlled by manipulating the amount of heat supplied to the feed stream and/or by manipulating the amount of the feed stream which is diverted as quench fluid so as to maintain a desired reaction temperature in the first reactor. The analysis of the amount of carbon monoxide in the feed stream flowing to the first reactor is utilized to bias the temperature control of the feed stream flowing to the first reactor.

An analysis of the product stream flowing from the second reactor provides an indication of the concentration of the acetylene in the product stream flowing from the second reactor. This concentration is compared to a desired concentration and the comparison is utilized to manipulate the temperature of the feed stream flowing from the first reactor to the second reactor by controlling the amount of the feed stream flowing from the first reactor to the second reactor which is utilized as a quench fluid. The control of the temperature of the feed stream flowing from the first reactor to the second reactor is also biased by the measurement of the concentration of the carbon monoxide in the feed stream flowing to the first reactor.

In this manner the required reaction temperatures are maintained in each reactor and a desired relationship between the amount of the acetylene hydrogenated in the first reactor and the amount of the acetylene hydrogenated in the second reactor can be maintained. Also a desired concentration of acetylene in the product stream from the second reactor can be maintained.

Other objects and advantages of the invention will be apparent from the description of the invention and the appended claims as well as from the detailed description of the drawing which is a schematic diagram of a selective hydrogenation process with an associated control system.

The invention is illustrated and described in terms of a selective hydrogenation process for the hydrogenation of acetylene in an ethylene product. However, it should be understood that this invention can be utilized for carrying out other selective hydrogenation processes such as the conversion of diolefins to olefinic and/or saturated compounds. The invention is also applicable to other processes, other than selective hydrogenation processes, for removing a constituent from a feed stream.

Although the invention is illustrated and described in terms of a specific hydrogenation process, the applicability of the invention described herein extends to other process configurations such as using different heat exchanger configurations, more than two reactors or as has been previously stated, two catalyst beds in a single reactor vessel. The invention also extends to different types of control system configurations which accomplish the purpose of the invention. Lines designated as signal lines in the drawings are pneumatic in this preferred embodiment. However, this invention is also applicable to electrical, mechanical, hydraulic or other signal means for transmitting information. In many control systems some combination of these types of signals will be used. However, use of any other type of signal transmission, compatible with the process and equipment in use, is within the scope of the invention.

Controllers shown may utilize the various modes of control such as proportional, proportional-integral, proportional-derivative or proportional-integral-derivative. In this preferred embodiment proportional-integral controllers are utilized. The operation of these types of controllers is well known in the art. The output control signal of a proportional-integral controller may be represented as $$S = K_1 E + K_2 \int E \, dt$$

where
S = output control signal;
E = difference between two input signals; and
$K_1$ and $K_2$ = constants.

The various transducing means used to measure parameters which characterize the process and the various signals generated thereby may take a variety of forms or formats. For example, the control elements of the system can be implemented using electrical analog, digital electronic, pneumatic, hydraulic, mechanical or other types of equipment or combinations of one or more of such equipment types. While the presently preferred embodiment of the invention preferably utilizes pneumatic control elements in conjunction with pneumatic signal handling and translation apparatus, the apparatus and method of the invention can be implemented using a variety of specific equipment available to and understood by those skilled in the process control art. Likewise, the format of the various signals can be modified substantially in order to accommodate signal format requirements of a particular installation, safety factors, the physical characteristics of the measuring or control instruments and other similar factors. For example, a measurement of a system parameter may exhibit a generally proportional relationship to the square of the actual system parameter. Other measuring instruments might produce a signal which is proportionl to the measured parameter, and still other measuring instruments may produce a signal which bears a more complicated, but known, relationship to the measured system parameter. In addition all signals could be translated into a "suppressed zero" or other similar format in order to provide a "live zero" and prevent an equipment failure from being erroneously interpreted as a low (or high) measurement or control signal. Regardless of the signal format or the exact relationship of the signal to the parameter which it represents, each signal representative of a measured process parameter or representative of a desired process value will bear a relationship to the measure parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to the drawing, an ethylene feed stream containing some concentration of acetylene and carbon monoxide is introduced through conduit means 8, 9 and 10 to the reactor 12 which contains a first catalyst bed containing a hydrogenation catalyst. Heat exchanger 14 is operably located between conduit means 9 and 10. Steam or another suitable heating fluid is provided through conduit means 17 to the heat exchanger 14 and is utilized to provide heat to the feed flowing through conduit means 8, 9 and 10. Heat exchanger 15 is operably located between conduit means 8 and 9. The product stream from the reactor 18, which flows through conduit means 19, is provided to the heat exchanger 15 and is also utilized to provide heat to the feed stream flowing through conduit means 8, 9 and 10. The pneumatic control valve 21 is operably located in conduit means 8 and is utilized to split the flow of the feed between conduit means 8 and the bypass conduit means 11. The feed flowing through conduit means 10 and the bypass conduit means 11 are preferably mixed before the feed enters the reactor 12. The feed flowing through the bypass conduit means 11 is utilized as a quench fluid to provide further temperature control of the feed flowing to the reactor 12.

The effluent flowing from the reactor 12 is passed through conduit means 22 and 23 to the reactor 18 which contains a second catalyst bed containing the hydrogenation catalyst. Heat exchanger 25 which is operably located between conduit means 22 and 23 is utilized to provide a means for cooling the effluent flowing through conduit means 22 and 23. A cooling fluid such as water is provided through conduit means 26 to the heat exchanger 25. The pneumatic control valve 28, which is operably located in conduit means 22, is utilized to control the relationship between the amount of effluent flowing from the reactor 12 which flows to the reactor 18 through the heat exchanger 25 and through the bypass conduit means 24. The effluent flowing through conduit means 24 may be considered the primary effluent stream and the effluent flowing through conduit means 22, the heat exchanger means 25, and conduit means 23 may be considered the quench fluid stream. The two fluid streams flowing through conduit means 24 and conduit means 23 are preferably mixed before entering the reactor 18.

The ethylene product, which will have a very low concentration of acetylene, is removed from the reactor 18 through conduit means 19. As has been previously stated the product removed through conduit means 19 from the reactor 18 flows through the heat exchanger 15 to provide heat to the feed flowing through conduit means 8, 9 and 10 to the reactor 12.

A sample of the feed flowing through conduit means 8 is passed through conduit means 32 to analyzer transducer 31, which is preferably a chromatographic analyzer. Analyzer transducer 31 provides two output signals in response to the analysis of the feed flowing through conduit means 8. Signal 33 is representative of the concentration of the carbon monoxide in the feed flowing through conduit means 8. Signal 34, from the analyzer transducer 31 is representative of the concentration of the acetylene in the feed flowing through conduit means 8. Signal 33 is provided from the analyzer transducer 31 to the multiplying means 36. Signal 34 is provided from the analyzer transducer 31 to the multiplying means 37.

Carbon monoxide tends to poison the hydrogenation catalyst. If the concentration of carbon monoxide in the feed flowing through conduit means 8 changes, the temperature required for the hydrogenation of acetylene in the reactors 12 and 18 also changes. The multiplying means 36 is supplied with a set point signal 38 which is representative of the change in temperature which is required for a given degree of change in the concentration of carbon monoxide in the feed flowing to conduit means 8. In the preferred embodiment of this invention the set point signal 38 is equal to 1° F./0.01 percent CO. Thus, if the concentration of carbon monoxide is 0.1 mol percent in the feed flowing through conduit means 8, the output signal 41 from the multiplying means 36 will be representative of 10° F. The output signal 41 from the multiplying means 36 provides a means for compensating for the concentration of carbon monoxide in the feed flowing through conduit means 8 by raising the temperature of the hydrogenation reaction in reactors 12 and 18 to compensate for the carbon monoxide concentration in the feed flowing through conduit means 8. It is noted that the concentration of carbon monoxide in the feed flowing through conduit means 8 will be essentially equal to the concentration of carbon monoxide flowing through the conduit means 22 from the reactor 12. Signal 41 from the multiplying means 36 is provided as a first input to the summing means 43 and to the summing means 44.

The multiplying means 37 is provided with a set point signal 46 which is representative of the desired relationship between the precentage of the total conversion of acetylene which is accomplished in reactor 12 and the percentage of the total conversion of acetylene which is accomplished in reactor 18. Thus, if it is desired that 75 percent of the conversion of the acetylene takes place in reactor 12 and 25 percent of the required conversion of acetylene takes place in reactor 18, signal 46 is representative of 25 percent. Preferably 70 to 80 percent of the acetylene is converted in reactor 12 with 20 to 30 percent of the acetylene being converted in reactor 18. Signal 34, which is representative of the concentration of acetylene in the feed flowing through conduit means 8, is multiplied by signal 46 to produce signal 48 which is output from the multiplying means 37. Signal 48 is equal to the desired concentration of acetylene in the effluent flowing from the reactor means 12 through conduit means 22. Signal 48 is provided as a first input to the analyzer controller 51.

A sample of the feed stream flowing through conduit means 22 is passed through conduit means 54 to the analyzer transducer 53, which is preferably a chromatographic analyzer. Analyzer transducer 53 provides an output signal 56 which is representative of the measured concentration of the acetylene in the effluent flowing through conduit means 22. Signal 56 is provided from the analyzer transducer 53 as a second input to the analyzer controller 51. The analyzer controller 51 compares signal 56 with signal 48. In response to this comparison the analyzer controller 51 provides an output signal 57 which is representative of the temperature change required to make the concentration of the acetylene in the effluent flowing through conduit means 22 equal to the desired concentration represented by signal 48. Signal 57 is supplied from the analyzer controller 51 as a second input to the summing means 44. In response to signal 41, the summing means 44 provides an output signal 59 which is representative of the desired temperature of the feed flowing through conduit means 10 into the reactor 12.

Temperature transducer 61 together with a temperature measuring instrument such as a thermocouple, which is located in conduit means 10, provides an output signal 63 which is representative of the measured temperature of the feed flowing through conduit means 10 into the reactor 12. This measurement is preferably obtained after the quench fluid flowing through conduit means 11 has been mixed with the feed flowing through conduit means 10. Signal 63 is provided as a second input to the temperature controller 65. The temperature controller 65 compares signal 63 and signal 59 to provide an output signal 68. Signal 68 is provided to the pneumatic control valve 69 which is operably located in conduit means 17 and is provided to the pneumatic control valve 21. Pneumatic control valves 69 and 21 are manipulated in response to signal 68 to thereby control the temperature of the feed flowing through conduit means 10 into the reactor 12.

Split range control is utilized to control the temperature of the feed flowing through conduit means 11 in the reactor 12. Pneumatic control valve 69 is fully open when signal 68 from the temperature controller 65 has a value less than or equal to 3 pounds. Pneumatic control valve 69 is fully closed when signal 68 has a value greater than or equal to 9 pounds. Pneumatic control valve 21 allows no feed to flow through conduit means 11 when the signal 68 is less than or equal to 9 pounds. Pneumatic control valve 21 diverts all of the feed flowing through conduit means 8 to conduit means 11 when signal 68 is greater than or equal to 15 pounds. Thus the feed flowing through conduit means 10 into the reactor 12 will have a maximum temperature when signal 68 has a value of 3 pounds or less and will have a minimum temperature when signal 68 has a value of 15 pounds or greater.

It is noted that this control of both the flow rate of the heating fluid through conduit means 17 and the split of the feed stream is preferable. However, either could be used as a stand alone control, if desired, to manipulate the temperature of the feed stream flowing through conduit means 10 to the reactor 12. Control of both provide a more responsive temperature control.

A sample of the feed stream flowing through conduit means 19 is passed through conduit means 72 to the analyzer transducer 71 which is preferably a chromatographic analyzer. Analyzer transducer 71 provides an output signal 74 which is representative of the acetylene concentration in the product stream flowing through conduit means 19. Signal 74 is provided from the analyzer transducer 71 as a first input to the analyzer controller 75. The analzyer controller 75 is also provided with a set point signal 77 which is representative of the desired acetylene concentration of the product flowing through conduit means 19. The analyzer controller 75 compares signal 74 with signal 77 to provide an output signal 78 which is representative of any change in the temperature of the feed flowing through conduit means 23 into reactor 18 required to maintain the acetylene concentration in the product flowing through conduit means 19 equal to the desired acetylene concentration represented by signal 77. Signal 78 is provided from the analyzer controller 75 as a second input to the summing means 43. In response to signal 78 which and signal 41, the summing means 43 provides an output signal 79 which is representative of the desired temperature of the feed flowing through conduit means 23 into the reactor 18.

Temperature transducer 81 together with a temperature measuring element such as a thermocouple, which is operably located in conduit means 23, provides an output signal 83 which is representative of the measured temperature of the effluent flowing through conduit means 23 into the reactor 18. Signal 83 is provided from the temperature transducer 81 as a second input to the temperature controller 84. In response to the comparison of signal 83 and signal 79, the temperature controller 84 provides an output control signal 86 to the pneumatic control valve 28. The pneumatic control valve 28 is manipulated in response to signal 86 to provide sufficient effluent from the reactor 12 to the cooling heat exchanger 25 to maintain the desired temperature of the effluent flowing through conduit means 23 into the reactor 18. In this preferred embodiment when signal 86 has a value equal to or less than 3 pounds, the pneumatic control valve 28 operates to completely bypass the cooling heat exchanger 25. When the control signal 86 has a value greater than or equal to 15 pounds the pneumatic control valve 28 operates to direct all of the effluent flowing from the reactor 12 to the reactor 18 through the cooling heat exchanger 25.

The invention has been described in terms of a control system for a selective hydrogenation process in which at least two catalyst beds are utilized. Independent control systems for each reactor or catalyst bed have been described. It is noted that, while it is preferable that the independent control systems be used together to control the selective hydrogenation process, each independent control system may be used either alone or in conjunction with another type of control system, if desired, to control the selective hydrogenation process illustrated in FIG. 1. However, used alone the independent control systems, illustrated in FIG. 1, do not give the close control of the selective hydrogenation process that is possible if both control systems are used together.

The invention has been described in terms of a presently preferred embodiment as is illustrated in FIG. 1. Specific components which can be used in the practice of the invention as illustrated in FIG. 1 such as pneumatic control valves 21, 28 and 69; temperature transducers 61 and 81; temperature controllers 51, 75, 65, and 84; multiplying means 36 and 37; and summing means 43 and 44 are each well known, commercially available control components such as are described at length in Perry's Chemical Engineers' Handbook, 4th Edition, Chapter 22, McGraw-Hill.

Analyzer transducers 31, 53 and 71 are preferably chromatographic analyzers such as the Model 102 Process Chromatograph System, manufactured by Applied Automation Inc., Bartlesville, Okla.

For reasons of brevity, conventional auxiliary equipment such as pumps, additional heat exchangers, additional measurement-control devices, etc. have not been included in the above description as they play no part in the explanation of the invention.

While the invention has been described in terms of the presently preferred embodiment, reasonable variations and modifications are possible by those skilled in the art, within the scope of the described invention and the appended claims. Variations such as utilizing the control system of the present invention in different selective hydrogenation processes or using more than two reactors is within the scope of the invention.

That which is claimed is:

1. Apparatus comprising:
    a first catalyst bed;
    means for supplying a first feed stream containing a first constituent to said first catalyst bed, at least a portion of said first constituent in said first feed stream being removed from said first feed stream in said first catalyst bed;
    a second catalyst bed;
    means for withdrawing the reaction effluent from said first catalyst bed as a first product stream and for supplying said first product stream as a second feed stream to said second catalyst bed, a least a portion of said first constituent in said second feed stream being removed from said second feed stream in said second catalyst bed;
    means for withdrawing the reaction effluent, containing a substantially reduced concentration of said first constituent, from said second catalyst bed as a second product stream;
    means for establishing a first signal representative of the concentration of said first constituent in said first feed stream;
    means for establishing a second signal representative of the percentage of said first constituent in said first feed stream which is desired to be in said first product stream;
    means, responsive to said first signal and said second signal, for establishing a third signal representative of the desired concentration of said first constituent in said first product stream;
    means for establishing a fourth signal representative of the actual concentration of said first constituent in said first product stream;
    means, responsive to said third signal and said fourth signal, for establishing a fifth signal representative of the temperature of said first feed stream necessary to maintain the desired concentration of said first constituent in said first product stream represented by said third signal;
    means for establishing a sixth signal representative of the actual temperature of said first feed stream;
    means for comparing said fifth signal and said sixth signal and for establishing a seventh signal reponsive to the difference between said fifth signal and said sixth signal; and
    means for manipulating the temperature of said first feed stream in response to said seventh signal.

2. Apparatus in accordance with claim 1 wherein said means for establishing said third signal comprises means for multiplying said first signal by said second signal.

3. Apparatus in accordance with claim 2 wherein said second signal has a value in the range of from about 20 percent to about 30 percent of the concentration of said first constituent in said first feed stream.

4. Apparatus in accordance with claim 1 wherein said means for establishing said fifth signal comprises means for comparing said third signal and said fourth signal and for establishing said fifth signal responsive to the difference between said third signal and said fourth signal.

5. Apparatus in accordance with claim 1 wherein said means for manipulating the temperature of said first feed stream in response to said seventh signal comprises:
a first heat exchanger means operably located in said means for supplying said first feed stream;
means for controlling the flow of a heating fluid to said first heat exchanger means in response to said seventh signal;
bypass conduit means for bypassing at least a portion of said first feed stream around said first heat exchanger means; and
means for manipulating the flow of said first feed stream through said bypass conduit means in response to said seventh signal.

6. Apparatus in accordance with claim 5 additionally comprising:
a second heat exchanger means operably located in said means for supplying said first feed stream; and
means for supplying said second product stream from said second catalyst bed as a heating fluid to said second heat exchanger means.

7. Apparatus in accordance with claim 5 additionally comprising:
means for establishing an eighth signal representative of the concentration of a second constituent in said first feed stream, said second constituent being a constituent which tends to poison the catalyst in said first and second catalyst beds;
means for establishing a ninth signal representative of the change in the temperature of said first feed stream required to compensate for a change in the concentration of said second constituent which is represented by said eighth signal;
means for combining said eighth signal and said ninth signal to establish a tenth signal representative of a required temperature change in said first feed stream; and
means for biasing said fifth signal with said tenth signal.

8. Apparatus in accordance with claim 7 wherein said means for establishing said tenth signal comprises means for multiplying said eighth signal by said ninth signal and wherein said means for biasing said fifth signal with said tenth signal comprises means for adding said tenth signal to said fifth signal.

9. Apparatus in accordance with claim 1 additionally comprising:
means for establishing an eighth signal representative of the concentration of said first constituent in said second product stream;
means for establishing a ninth signal representative of the desired concentration of said first constituent in said second product stream;
means, responsive to said eighth signal and said ninth signal, for establishing a tenth signal representative of the temperature of said second feed stream necessary to maintain the desired concentration of said first constituent in said second product stream represented by said ninth signal;
means for establishing an eleventh signal representative of the actual temperature of said first product stream flowing to said second catalyst bed;
means for comparing said tenth signal and said eleventh signal and for establishing a twelfth signal responsive to the difference between said tenth signal and said eleventh signal; and
means for manipulating the temperature of said second feed stream in response to said twelfth signal.

10. Apparatus in accordance with claim 9 wherein said means for establishing said tenth signal comprises means for comparing said eighth signal and said ninth signal and for establishing said tenth signal responsive to the difference between said eighth signal and said ninth signal.

11. Apparatus in accordance with claim 9 wherein said means for manipulating the temperature of said second feed stream in response to said twelfth signal comprises:
a heat exchanger means operably located in said means for supplying said second feed stream;
means for supplying a cooling fluid to said heat exchanger means;
bypass conduit means for bypassing said second feed stream around said heat exchanger means; and
means for manipulating the flow of said second feed stream through said bypass conduit means in response to said twelfth signal.

12. Apparatus in accordance with claim 11 additionally comprising:
means for establishing a thirteenth signal representative of the concentration of a second constituent in said second feed stream, said second constituent being a constituent which tends to poison the catalyst in said first and second catalyst beds;
means for establishing a fourteenth signal representative of the change in the temperature of said second feed stream required to compensate for a change in the concentration of said second constituent which is represented by said thirteenth signal;
means for combining said thirteenth signal and said fourteenth signal to establish a fifteenth signal representative of a required temperature change in said second feed stream; and
means for biasing said tenth signal with said fifteenth signal.

13. Apparatus in accordance with claim 12 wherein said means for establishing said fifteenth signal comprises means for multiplying said thirteenth signal by said fourteenth signal and wherein said means for biasing said tenth signal with said fifteenth signal comprises means for adding said fifteenth signal to said tenth signal.

14. Apparatus comprising:
a first catalyst bed;
means for supplying a first feed stream containing a first constituent to said first catalyst bed, at least a portion of said first constituent in said first feed stream being removed from said first feed stream in said first catalyst bed;
a second catalyst bed;
means for withdrawing the reaction effluent from said first catalyst bed as a first product stream and for supplying said first product stream as a second feed stream to said second catalyst bed, at least a portion of said first constituent in said second feed stream being removed from said second feed stream in said second catalyst bed;
means for withdrawing the reaction effluent, containing a substantially reduced concentration of said first constituent, from said second catalyst bed as a second product stream;

means for establishing a first signal representative of the concentration of said first constituent in said second product stream;

means for establishing a second signal representative of the desired concentration of said first constituent in said second product stream;

means, responsive to said first signal and said second signal, for establishing a third signal representative of the temperature of said second feed stream necessary to maintain the desired concentration of said first constituent in said second product stream represented by said second signal;

means for establishing a fourth signal representative of the actual temperature of said second feed stream flowing to said second catalyst bed;

means for comparing said third signal and said fourth signal and for establishing a fifth signal responsive to the difference between said third signal and said fourth signal; and means for manipulating the temperature of said second feed stream in response to said fifth signal.

15. Apparatus in accordance with claim 14 wherein said means for establishing said third signal comprises means for comparing said first signal and said second signal and for establishing said third signal responsive to the difference between said first signal and said second signal.

16. Apparatus in accordance with claim 14 wherein said means for manipulating the temperature of said second feed stream in response to said fifth signal comprises;
a heat exchanger means operably located in said means for supplying said second feed stream;
means for supplying a cooling fluid to said heat exchanger means;
bypass conduit means for bypassing said second feed stream around said heat exchanger means; and
means for manipulating the flow of said second feed stream through said bypass conduit means in response to said fifth signal.

17. Apparatus in accordance with claim 16 additionally comprising:
means for establishing a sixth signal representative of the concentration of a second constituent in said second feed stream, said second constituent being a constituent which tends to poison the catalyst in said first and second catalyst beds;
means for establishing a seventh signal representative of the change in the temperature of said second feed stream required to compensate for a change in the concentration of said second constituent which is represented by said sixth signal;
means for combining said sixth signal and said seventh signal to establish an eighth signal representative of a required temperature change in said second feed stream; and
means for biasing said fifth signal with said eighth signal.

18. Apparatus in accordance with claim 17 wherein said means for establishing said eighth signal comprises means for multiplying said sixth signal by said seventh signal and wherein said means for biasing said fifth signal with said eighth signal comprises means for adding said eighth signal to said fifth signal.

19. A method for removing a first constituent in a feed stream, wherein said feed stream is supplied to at least two reaction zones in series, comprising the steps of:

establishing a first signal representative of the concentration of said first constituent in said feed stream being supplied to the first reaction zone of said at least two reaction zones in series;

establishing a second signal representative of the percentage of said first constituent, in said feed stream flowing to said first reaction zone, which should be removed in said first reaction zone;

establishing a third signal representative of the desired concentration of said first constituent in said feed stream flowig from said first reaction zone to the second reaction zone of said at least two reaction zones in series in response to said first signal and said second signal;

establishing a fourth signal representative of the actual concentration of said first constituent in the feed stream flowing from said first reaction zone to said second reaction zone;

establishing a fifth signal, representative of the temperature of said feed stream entering said first reaction zone necessary to maintain the desired concentration of said first constituent in the feed stream flowing from said first reaction zone to said second reaction zone, in response to said third signal and said fourth signal;

establishing a sixth signal representative of the actual temperature of the feed stream flowing to said first reaction zone;

comparing said fifth signal and said sixth signal and establishing a seventh signal responsive to the difference between said fifth signal and said sixth signal; and manipulating the temperature of said feed stream flowing to said first reaction zone in response to said seventh signal.

20. A method in accordance with claim 19 wherein said step of establishing said third signal comprises multiplying said first signal by said second signal.

21. A method in accordance with claim 20 wherein said second signal has a value in the range of from about 20 percent to about 30 percent of the concentration of said first constituent in the feed stream flowing to said first reaction zone.

22. A method in accordance with claim 19 wherein said step of establishing said fifth signal comprises comparing said third signal and said fourth signal and establishing said fifth signal responsive to the difference between said third signal and said fourth signal.

23. A method in accordance with claim 19 wherein said step of manipulating the temperature of said feed stream being supplied to said first reaction zone in response to said seventh signal comprises:
splitting the flow of said feed stream to said first reaction zone in such a manner that a first portion of the flow of said feed stream flowing to said first reaction zone is passed through a first heat exchanging zone to said first reaction zone and a second portion of said feed stream flowing to said first reaction zone is passed directly to said first reaction zone;
controlling the flow of a heating fluid to said first heat exchanging zone in response to said seventh signal in such a manner that a maximum supply of said heating fluid is supplied to said first heat exchanging zone when maximum heating is desired for said feed stream flowing to said first reaction zone and a minimum supply of said heating fluid is supplied to said first heat exchanging zone when a temperature equal to or below a medium temperature is desired for the feed stream flowing to said first reaction zone, said medium temperature being a temperature between said maximum for said feed stream flowing to said first reaction zone and a minimum temperature for said feed stream flowing to said first reaction zone; and controlling the flow of the second portion of said feed stream flowing to said first reaction zone in such a manner that substantially all of said feed stream flowing to said first reaction zone is supplied with the second portion of said feed stream flowing to said first reaction zone when said minimum temperature is desired for said feed stream flowing to said first reaction zone and substantially all of the feed stream is supplied as the first portion of said feed stream when a temperature equal to or greater than said medium temperature is desired for said feed stream flowing to said first reaction zone.

24. A method in accordance with claim 23 wherein a product stream from said second reaction zone is supplied to a second heat exchanging zone to supply heat to the first portion of said feed stream flowing to said first reaction zone.

25. A method in accordance with claim 23 comprising the additional steps of:
establishing an eighth signal respresentative of the concentration of a second constituent in said feed stream flowing to said first reaction zone, said second constituent being a constituent which tends to poison the catalyst in said first and second reaction zones;
establishing a ninth signal representative of the change in the temperature of said feed stream flowing to said first reaction zone required to compensate for a change in the concentration of said second constituent;
establishing a tenth signal, representative of a required temperature change in said feed stream flowing to said first reaction zone, in response to said eighth signal and said ninth signal; and
biasing said fifth signal with said tenth signal.

26. A method in accordance with claim 25 wherein said step of establishing said tenth signal comprises multiplying said eighth signal by said ninth signal and wherein said step of biasing said fifth signal with said tenth signal comprises adding said tenth signal to said fifth signal.

27. A method in accordance with claim 19 comprising the additional steps of:
establishing an eighth signal representative of the concentration of said first constituent in a product stream flowing from said second reaction zone;
establishing a ninth signal representative of the desired concentration of said first constituent in said product stream flowing from said second reaction zone;
establishing a tenth signal, representative of the temperature of said feed stream flowing from said first reaction zone to said second reaction zone, necessary to maintain the desired concentration of said first constituent in said product stream flowing from said second reaction zone, in response to said eighth signal and said ninth signal;
establishing an eleventh signal representative of the actual temperature of said feed stream flowing from said first reaction zone to said second reaction zone;
comparing said tenth signal and said eleventh signal and establishing a twelfth signal responsive to the difference between said tenth signal and said eleventh signal; and
manipulating the temperature of said feed stream flowing from said first reaction zone to said second reaction zone in response to said twelfth signal.

28. A method in accordance with claim 27 wherein said step of establishing said tenth signal comprises comparing said eighth signal and said ninth signal and establishing said tenth signal responsive to the difference between said eighth signal and said ninth signal.

29. A method in accordance with claim 27 wherein said step of manipulating the temperature of the feed stream flowing from said first reaction zone to said second reaction zone in response to said twelfth signal comprises:
splitting the flow of said feed stream flowing from said first reaction zone to said second reaction zone in such a manner that a first portion of the flow of said feed stream flowing from said first reaction zone to said second reaction zone is passed through a heat exchanging zone to said second reaction zone and a second portion of said feed stream flowing from said first reaction zone to said second reaction zone is passed directly to said second reaction zone, said heat exchanging zone having a cooling fluid supplied thereto;
controlling the flow of the second portion of said feed stream flowing from said first reaction zone to said second reaction zone in response to said tenth signal in such a manner that substantially all of the feed stream being supplied to said second reaction zone is supplied with the second portion of the feed stream flowing from said first reaction zone to said second reaction zone when a maximum temperature is desired for the feed stream entering said second reaction zone and substantially all of the feed stream flowing from said first reaction zone to said second reaction zone is supplied as the first portion of the feed stream flowing from said first reaction zone to said second reaction zone when maximum cooling is desired for the feed stream entering said second reaction zone.

30. A method in accordance with claim 29 comprising the additional steps of:
establishing a thirteenth signal representative of the concentration of a second constituent in said feed stream flowing from said first reaction zone to said second reaction zone, said second constituent being a constituent which tends to poison the catalyst in said first and second reaction zones;
establishing a fourteenth signal representative of the change in the temperature of said feed stream flowing from said first reaction zone to said second reaction zone required to compensate for a change in the concentration of said second constituent;
establishing a fifteenth signal, representative of a required temperature change in said feed stream flowing from said first reaction zone to said second reaction zone, in response to said thirteenth signal and said fourteenth signal; and
biasing said tenth signal with said fifteenth signal.

31. A method in accordance with claim 30 wherein said step of establishing said fifteenth signal comprises multiplying said thirteenth signal by said fourteenth signal and wherein said step of biasing said tenth signal with said fifteenth signal comprises adding said fifteenth signal to said tenth signal.

32. A method for removing a first constituent in a feed stream wherein said feed stream is supplied to at least two reaction zones in series, comprising the steps of:

establishing a first signal representative of the concentration of said first constituent in a product stream flowing from the second reaction zone of said at least two reaction zones in series;

establishing a second signal representative of the desired concentration of said first constituent in said product stream flowing from said second reaction zone;

establishing a third signal, representative of the temperature of a feed stream flowing from the first reaction zone, of said at least two reaction zones in series, to said second reaction zone, necessary to maintain the desired concentration of said first constituent in said product stream flowing from said second reaction zone, in response to said first signal and said second signal;

establishing a fourth signal representative of the actual temperature of said feed stream flowing from said first reaction zone to said second reaction zone;

comparing said third signal and said fourth signal and establishing a fifth signal responsive to the difference between said third signal and said fourth signal; and manipulating the temperature of said feed stream flowing from said first reaction zone to said second reaction zone in response to said fifth signal.

33. A method in accordance with claim 32 wherein said step of establishing said third signal comprises comparing said first signal and said second signal and establishing said third signal responsive to the difference between said first signal and said second signal.

34. A method in accordance with claim 32 wherein said step of manipulating the temperature of the feed stream flowing from said first reaction zone to said second reaction zone in response to said fifth signal comprises:

splitting the flow of said feed stream flowing from said first reaction zone to said second reaction zone in such a manner that a first portion of the flow of said feed stream flowing from said first reaction zone to said second reaction zone is passed through a heat exchanging zone to said second reaction zone and a second portion of said feed stream flowing from said first reaction zone to said second reaction zone is passed directly to said second reaction zone, said heat exchanging zone having a cooling fluid supplied thereto;

controlling the flow of the second portion of said feed stream flowing from said first reaction zone to said second reaction zone in response to said fifth signal in such a manner that substantially all of the feed stream flowing to said second reaction zone is supplied with the second portion of the feed stream flowing from said first reaction zone to said second reaction zone when a maximum temperature is desired for the feed stream entering said second reaction zone and substantially all of the feed stream flowing to said second reaction zone is supplied as the first portion of the feed stream flowing from said first reaction zone to said second reaction zone when maximum cooling is desired for the feed stream entering said second reaction zone.

35. A method in accordance with claim 34 comprising the additional steps of:

establishing a sixth signal representative of the concentration of a second constituent in the feed stream flowing to said first reaction zone, said second constituent being a constituent which tends to poison the catalyst in said first and second reaction zones;

establishing a seventh signal representative of the change in the temperature of said feed stream flowing from said first reaction zone to said second reaction zone required to compensate for a change in the concentration of said second constituent;

establishing an eighth signal, representative of a required temperature change in said feed stream flowing from said first reaction zone to said second reaction zone in response to said sixth signal and said seventh signal; and biasing said third signal with said eighth signal.

36. A method in accordance with claim 35 wherein said step of establishing said eighth signal comprises multiplying said sixth signal by said seventh signal and wherein said step of biasing said third signal with said eighth signal comprises adding said eighth signal to said third signal.

* * * * *